United States Patent [19]

Pelosi, Jr.

[11] 4,012,414
[45] Mar. 15, 1977

[54] 2-(5-PHENYL-2-FURYL)IMIDAZOLES
[75] Inventor: Stanford S. Pelosi, Jr., Norwich, N.Y.
[73] Assignee: Morton-Norwich Products, Inc., Norwich, N.Y.
[22] Filed: Jan. 29, 1976
[21] Appl. No.: 653,295
[52] U.S. Cl. .............................. 260/309; 424/273; 260/346.1 R; 260/347.7
[51] Int. Cl.² ..................................... C07D 405/04
[58] Field of Search ................................... 260/309
[56] References Cited
UNITED STATES PATENTS 2,710,870  6/1955  Lawson ............................. 260/309
3,600,399  8/1971  Berkelhammer et al. ......... 260/309

FOREIGN PATENTS OR APPLICATIONS 1,215,858  12/1970  United Kingdom ................ 260/309

OTHER PUBLICATIONS

Schubert et al., Chem. Abst., 1963, vol. 58, cols. 2445–2446.

*Primary Examiner*—Natalie Trousof
*Attorney, Agent, or Firm*—Anthony J. Franze

[57]  ABSTRACT

A series of 2-(5-phenyl-2-furyl)imidazoles are useful as antidepressants.

6 Claims, No Drawings

2-(5-PHENYL-2-FURYL)IMIDAZOLES

This invention is concerned with a series of 2-(5-phenyl-2-furyl) imidazoles of the formula:

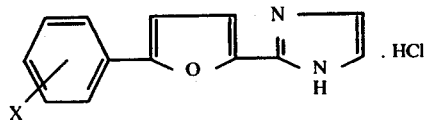

wherein X represents hydrogen, 2-nitro, 4-nitro, 4-amino, and 4-acetyl. These compounds are useful as antidepressants. Their useful antidepressant activity is exhibited in warm blooded animals under the standard ptosis-antitetrabenazine test. Thus, when administered perorally in suspension or aqueous solution in doses ranging from 50 to 200 mg/kg to mice shortly prior to intraperitoneal administration of from 1–10 mg/kg of tetrabenazine, ptosis induced by tetrabenazine is curtailed to the extent of from 46–100%.

The 2-(5-phenyl-2-furyl)imidazoles of this invention are prepared as illustrated in the following schema:

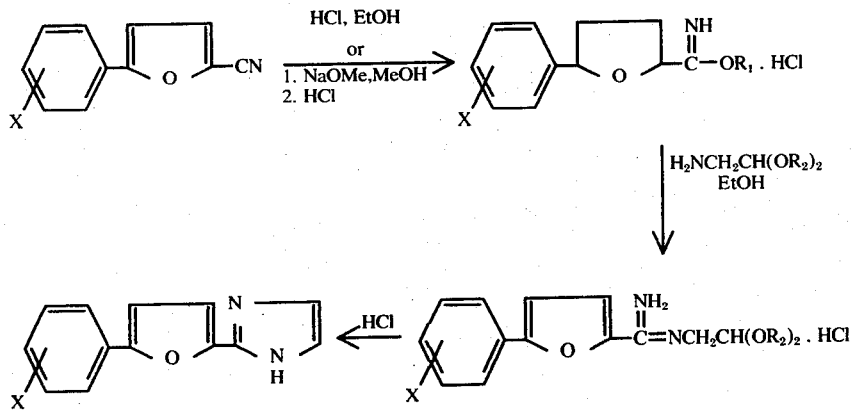

In the above schema, X has the significance previously ascribed, $R_1$ is methyl or ethyl, and $R_2$ is methyl or ethyl.

The preparation of the 2-(5-phenyl-2-furyl) imidazoles of this invention is more fully described in the following examples.

EXAMPLE I

2-[5-(4-Nitrophenyl)-2-furyl]imidazole Hydrochloride Tetartohydrate

A solution of 98 g (0.33 mole) of ethyl 5-(4-nitrophenyl)-2-furimidate hydrochloride and 48 g (0.36 mole) of aminoacetaldehyde diethyl acetal in 1500 ml of absolute ethanol was heated under reflux for 4 hr. After standing in a refrigerator for 2 days, the solid which was deposited was collected by filtration and washed with anhydrous ether to give 38 g (30%) of N-(2,2-diethoxyethyl)-5-(4-nitrophenyl)-2-furamidine hydrochloride. The filtrate was concentrated on a rotary evaporator. The solid which was deposited was collected by filtration and washed with anhydrous ether to give 34 g (57% total yield) of additional product, m.p. 220°–280° (dec.)

Anal. Calc'd. for $C_{17}H_{21}N_3O_5.HCl$: C, 53.19; H, 5.78; N, 10.95. Found: C, 53.34; H, 5.70; N, 10.90.

A mixture of 45 g (0.12 mole) of the above amidine and 450 ml of 3N HCl was stirred at 60°–70° for 24 hr and cooled in a refrigerator overnight. The yellow solid was collected by filtration, washed with water, air-dried, crushed in a mortar, and dried in a vacuum desiccator to give 34 g (100%) of product. An analytical sample was prepared by drying overnight in vacuo at the temperature of refluxing $CHCl_3$, m.p. 235°–280° (dec.).

Anal. Calc'd. for $C_{13}H_9N_3O_3HCl.¼ H_2O$: C, 52.71; H, 3.57; N, 14.19; $H_2O$, 1.5. Found: C, 52.65; H, 3.59; N, 14.08; $H_2O$, 0.86

EXAMPLE II

2-[5-(4-Aminophenyl)-2-furyl]imidazole Hydrochloride

A mixture of 17 g (0.057 mole) of the compound of Example I, 200 ml of $CH_3OH$ and 1 teaspoon of 5% Pd/C (50% $H_2O$) was shaken on a Parr apparatus with the theoretical amount of hydrogen being absorbed. The mixture was heated to reflux and $CH_3OH$ added to dissolution. The catalyst was removed by filtration and the filtrate cooled and diluted with ether. The resulting solid was recrystallized from anhydrous methanol and dried at 110° to yield 7 g (46%). An analytical sample was prepared by drying a sample in the vacuum pistol at the temperature of refluxing dimethylformamide, m.p. 242°–245°.

Anal. Calc'd. for $C_{13}H_{11}N_3O.HCl$: C, 59.66; H, 4.62; N, 16.06. Found: C, 59.35; H, 4.73; N, 15.99.

EXAMPLE III

2-[5-(2-Nitrophenyl)-2-furyl]imidazole Hydrochloride

A mixture of 5-(2-nitrophenyl)-2-furonitrile (92 g, 0.43 mole) and anhydrous methanol (1000 ml) was heated to 55° and sodium methoxide (1.5 g) was added. The steam bath was removed, the solution was stirred for 2 hours and stored overnight at room temperature. The solution was poured into ice water (1000 ml) and stirred for 1 hour. The methyl 5-(2-nitrophenyl)-2-furimidate was collected by filtration and air dried, yield: 91 g (86%). A sample was recrystallized from isopropanol, m.p. 107°–108°.

Anal. Calc'd. for $C_{12}H_{10}N_2O_4$: C, 58.54; H, 4.09; N, 11.38. Found: C, 58.56; H, 3.87; N, 11.26.

Gaseous HCl was introduced into anhydrous ether (600 ml) to saturation. The above imidate (53 g. 0.23 mole) was introduced in small increments and stirring was continued for 3 hr. After filtering and washing with anhydrous ether, the solid (66 g) was dried over KOH in a desiccator. A mixture of the above imidate hydrochloride (109 g, 0.39 mole), absolute alcohol (1600 ml), and aminoacetaldehyde dimethyl acetal (42 g, 0.4 mole) was refluxed for 3 hr. The solvent was removed in a rotary evaporator and the residue was dissolved in 3N HCl (1550 ml). This solution was heated (60°–73° C) for 20 hr. The content of the flask was ice cooled, and the solid was filtered and washed with water yielding 96 g (85%). An analytical sample (m.p. 267°–268°) was prepared by recrystallization from SDA No. 32.

Anal. Calc'd. for $C_{13}H_9N_3O_3 \cdot HCl$: C, 53.53; H, 3.46; N, 14.41. Found: C, 53.38; H, 3.10; N, 14.49.

EXAMPLE IV 2-(5-Phenyl-2-furyl)imidazole Hydrochloride

A mixture of 5-phenyl-2-furonitrile (30 g, 0.18 mole) and anhydrous methanol (500 ml) was heated to 45° C. Sodium methoxide (0.5 g) was introduced and stirring was continued for 4 hr. yielding a solution. It was poured into ice water (ca. 3.5 L). The material was filtered, washed with water and dried in a desiccator over KOH. It was introduced in small increments into anhydrous ether saturated with gaseous HCl. After stirring for several hours, the solid (33 g) (78%) was filtered.

A mixture of methyl 5-phenyl-2-furimidate hydrochloride (33 g, 0.14 mole), absolute alcohol (500 ml) and aminoacetaldehyde dimethyl acetal (15 g, 0.14 mole) was refluxed for 3 hr. The solvent was removed in a rotary evaporator and the residue was heated for 20 hr. at 63°–73° C with 3N HCl (400 ml). The solvent was decanted and the black viscous material was washed with water. It was purified by stirring with boiling acetonitrile and collected by filtration to give 4.1 g (9%). An analytical sample was prepared by recrystallization from acetonitrile m.p. >277° dec.

Anal. Calc'd. for $C_{13}H_{10}N_2O \cdot HCl$: C, 63.29; H, 4.43; N, 11.36. Found: C, 63.08; H, 4.42; N, 11.40.

EXAMPLE V

2-[5-(4-Acetylphenyl)-2-furyl]imidazole Hydrochloride

A mixture of 30 g (0.12 mole) of methyl 5-(4-acetylphenyl)-2-furimidate and 500 ml of saturated ethereal/HCl was stirred for 2 hrs. at room temperature and the resulting solid filtered. A mixture of this solid, 12.6 g (0.12 mole) of aminoacetaldehyde dimethyl acetal and 500 ml of methanol was refluxed for 3 hr. with the resulting solution being treated with Darco and filtered hot. The filtrate was taken to dryness on the Calab evaporator yielding a residual solid. This solid was dissolved in refluxing methanol (Darco), filtered and the filtrate cooled to room temperature. The filtrate was diluted with ether and the resulting solid filtered and air dried to yield 24 g (57%) of 5-(4-acetylphenyl)-N'-2,2-dimethoxyethyl-2-furamidine hydrochloride.

A mixture of 24 g (0.068 mole) of the above solid, and 500 ml of 3N hydrochloric acid was heated at 90°–95° for 4 hrs. The resulting near solution was treated with Darco and filtered. The filtrate upon cooling yielded a solid which was recrystallized from methanol (Darco) and dried at 110° to yield 11 g (51%). An analytical sample was prepared by drying a sample overnight in the vacuum pistol at the temperature of refluxing DMF, m.p. ca. 265°.

Anal. Calc'd. for $C_{15}H_{12}N_2O_2 \cdot HCl$. C, 62.40; H, 4.54; N, 9.70. Found: C, 62.59; H, 4.60; N, 9.69.

What is claimed is:

1. A compound of the formula:

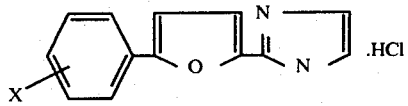

wherein X represents hydrogen, 2-nitro, 4-nitro, 4-amino, and 4-acetyl.

2. The compound 2-[5-(4-nitrophenyl)-2-furyl]imidazole hydrochloride.

3. The compound 2-[5-(4-aminophenyl)-2-furyl]imidazole hydrochloride.

4. The compound 2-[5-(2-nitrophenyl)-2-furyl]imidazole hydrochloride.

5. The compound 2-(5-phenyl-2-furyl)imidazole hydrochloride.

6. The compound 2-[5-(4-acetylphenyl)-2-furyl]imidazole hydrochloride.

* * * * *